United States Patent
Han et al.

(10) Patent No.: US 12,414,728 B2
(45) Date of Patent: Sep. 16, 2025

(54) ASYSTOLE DETECTION FOR CARDIOPULMONARY RESUSCITATION

(71) Applicant: KONINKLIJKE PHILIPS N.V., Eindhoven (NL)

(72) Inventors: Chengzong Han, Andover, MA (US); Saeed Babaeizadeh, Arlington, MA (US)

(73) Assignee: Koninklijke Philips N.V., Eindhoven (NL)

( * ) Notice: Subject to any disclaimer, the term of this patent is extended or adjusted under 35 U.S.C. 154(b) by 1314 days.

(21) Appl. No.: 15/109,488

(22) PCT Filed: Dec. 17, 2014

(86) PCT No.: PCT/IB2014/067016
§ 371 (c)(1),
(2) Date: Jul. 1, 2016

(87) PCT Pub. No.: WO2015/101878
PCT Pub. Date: Jul. 9, 2015

(65) Prior Publication Data
US 2016/0331260 A1    Nov. 17, 2016

Related U.S. Application Data

(60) Provisional application No. 61/922,890, filed on Jan. 2, 2014.

(51) Int. Cl.
*A61B 5/364* (2021.01)
*A61B 5/00* (2006.01)
(Continued)

(52) U.S. Cl.
CPC .............. *A61B 5/364* (2021.01); *A61B 5/347* (2021.01); *A61B 5/361* (2021.01); *A61B 5/4836* (2013.01);
(Continued)

(58) Field of Classification Search
CPC .... A61N 1/39; A61N 1/39044; A61N 1/3987; A61N 1/3925
See application file for complete search history.

(56) References Cited

U.S. PATENT DOCUMENTS 5,391,187 A * 2/1995 Freeman .............. A61N 1/3904
607/5
5,571,142 A * 11/1996 Brown ................. A61N 1/3925
128/200.24
(Continued)

FOREIGN PATENT DOCUMENTS

WO    2012176098 A1    12/2012

OTHER PUBLICATIONS

Jette, D.U., et al., "A qualitative study of clinical decision making in recommending discharge placement from teh acute care setting", Phys Ther. Mar. 2003, 83(3): Abstract.
(Continued)

*Primary Examiner* — Jennifer Pitrak McDonald
*Assistant Examiner* — Jennifer L Ghand (57) ABSTRACT

A patient monitoring device (20) employing an ECG monitor (24) and a controller (26). In operation, the ECG monitor (24) monitors a corrupted ECG waveform (30), and the controller (26) classifies the corrupted ECG waveform (30) as one of a non-shockable rhythm or a potentially shockable rhythm. The corrupted ECG waveform (30) is classified by the controller (26) as the non-shockable rhythm responsive to a detection by the controller (26) of a presence of an asystole rhythm within the corrupted ECG waveform (30). Conversely, the corrupted ECG waveform (30) is classified by the controller (26) as the potentially shockable rhythm responsive to a detection by the controller (26) of an absence of the asystole rhythm within the corrupted ECG waveform (30) or an indetermination by the controller (26) as to the
(Continued)

presence of the asystole rhythm within the corrupted ECG waveform (30).

20 Claims, 10 Drawing Sheets

(51) Int. Cl.
    *A61B 5/347*     (2021.01)
    *A61B 5/361*     (2021.01)
    *A61H 31/00*     (2006.01)
    *A61N 1/39*     (2006.01)

(52) U.S. Cl.
    CPC .......... *A61B 5/7207* (2013.01); *A61B 5/7217* (2013.01); *A61B 5/7221* (2013.01); *A61H 31/005* (2013.01); *A61N 1/39044* (2017.08); *A61N 1/3925* (2013.01); *A61N 1/3987* (2013.01)

(56) References Cited

U.S. PATENT DOCUMENTS

| | | |
|---|---|---|
| 5,957,856 A | 9/1999 | Weil et al. |
| 6,304,773 B1 * | 10/2001 | Taylor ..................... A61N 1/39 |
| | | 600/515 |
| 7,766,828 B2 | 8/2010 | Ishii et al. |
| 8,983,588 B2 | 3/2015 | Addison et al. |
| 9,339,436 B2 | 5/2016 | Freeman et al. |
| 9,616,244 B2 | 4/2017 | Anderson et al. |
| 9,955,913 B2 | 5/2018 | Freeman |
| 2004/0172068 A1 * | 9/2004 | Sullivan ............... A61N 1/3904 |
| | | 607/5 |
| 2006/0217624 A1 * | 9/2006 | Myklebust ........... A61N 1/3925 |
| | | 600/512 |
| 2010/0114219 A1 * | 5/2010 | Stickney .............. A61B 5/0809 |
| | | 607/5 |
| 2011/0082510 A1 | 4/2011 | Sullivan |
| 2011/0202101 A1 | 8/2011 | Tan et al. |
| 2011/0224746 A1 | 9/2011 | Didon |
| 2013/0296727 A1 | 11/2013 | Sullivan et al. |
| 2013/0325515 A1 | 12/2013 | Nikolova-Simons et al. |
| 2014/0207012 A1 | 7/2014 | Coult et al. |
| 2016/0188824 A1 | 6/2016 | Geleijnse et al. |

OTHER PUBLICATIONS

Guidelines focus on minimizing "hands off time", guidelines and European Resuscitation Council, American Heart Association.

* cited by examiner

ASYSTOLE DETECTION FOR CARDIOPULMONARY RESUSCITATION

This application is a national stage application under 35 U.S.C. § 371 of International Application No. PCT/IB2014/067016 filed on Dec. 17, 2014 and published in the English language on Jul. 9, 2015 as International Publication No. WO 2015/101878, which claims priority to U.S. Application No. 61/922,890 filed on Jan. 2, 2014, the entire disclosures of which are incorporated herein by reference.

The present invention generally relates to monitoring of cardiopulmonary resuscitation ("CPR") of a patient by an Automatic External Defibrillator ("AED"), an Advanced Life Support ("ALS") defibrillator/monitor, patient monitor and/or other medical devices having patient monitoring and/or defibrillation functionality. The present invention specifically relates to detecting asystole, a non-shockable rhythm, during CPR of a cardiac arrest patient.

Generally, automatic analysis of an ECG rhythm for sudden cardiac arrest patients during CPR may be unreliable due to a chest compression ("CC") artifact on an ECG waveform. Techniques have been proposed to filter the CC artifact to enable automated shock advisory during CPR. However, during non-shockable rhythms, in particular asystole rhythms, filtering residuals of the CC artifact may make the shock advisory algorithm to erroneously call the rhythm shockable because the filtering residuals or mechanically-induced electrical activity may look like a shockable rhythm to the shock advisory algorithm.

More particularly, a defibrillation shock is advised only to the patients who have specific shockable rhythms (e.g., ventricular fibrillation ("VF") or ventricular tachycardia ("VT")). Defibrillation is delivered using an AED or automatic mode of an ALS defibrillator/monitor, which automatically analyze the ECG to indicate if a shock is needed, or using manual defibrillators, including ALS defibrillator/monitors typically operated by medical practitioners or other trained users. In current practice, chest compression during CPR has to be interrupted for automated rhythm analysis by the AED or ALS defibrillator/monitor, because most shock advisory algorithms cannot reliably analyze the rhythm during chest compression. This is mainly because the mechanical activity from the chest compression introduces CC artifact to the ECG waveform which makes determining the underlying rhythm technically very difficult.

However, interrupting CPR for a reliable rhythm analysis by the AED may adversely affect the probability of survival of a patient in cardiac arrest. Both American Heart Association ("AHA") guidelines and European Resuscitation Council ("ERC"-) guidelines focus on minimizing "hands-off time", which is a time interval a patient in cardiac arrest is not receiving chest compressions. The primary device-related cause of CC interruption is automated ECG rhythm analysis for accurate shock advisory. The mechanical activity of chest compression produces CC artifact on the ECG waveform that most automated ECG analysis programs cannot fully differentiate from the patient's inherent ECG morphology. Furthermore, clinicians observing an ECG waveform on the AED's display cannot see the patient's underlying rhythm through the electrical noise created by the chest compression, which forces an interruption to the chest compression for rhythm assessment.

Recently, reliable rhythm analysis without interrupting chest compression has become an active research field in the hope of improving the survival rate of sudden cardiac arrest patients. Several methods have been proposed to analyze the ECG waveform during chest compression. For example, some algorithms are based on features obtained directly from the ECG waveform corrupted by the CC artifact, while other algorithms first filter the CC artifact out of ECG waveform and then classify the filtered ECG using a shock advisory algorithm.

Methods based on filtering CC artifact are reported to present better results than methods based on the analysis of the CC-corrupted ECG. However, a limitation of such filter-based techniques is that imperfect filtering of CC artifact can leave some residuals on the ECG waveform, which can potentially lead to incorrect determination of the underlying rhythm by the shock advisory algorithm. Furthermore, even if it was possible to perfectly filter out every bit of CC artifact out of the ECG waveform, there is evidence that the mechanical activity performed on the chest during chest compression can cause electrical activity on the heart which could be confused with VF by shock advisory algorithms.

Furthermore, delivering a shock is not advised to patients with asystole rhythm, and imperfect filtering of CC artifact from asystole rhythm can leave residuals on the ECG waveform which can look like VF. Furthermore, mechanical activity during CC can introduce some VF-like electrical activity on the ECG waveform. Therefore, filter-based shock advisory techniques, which try to analyze the ECG waveform without interrupting chest compression, have a weakness in accurately detecting asystole rhythm of the ECG waveform. Consequently, such shock advisory techniques can erroneously advise shock for asystole rhythm, which is not recommended by the AHA and ERC guidelines.

The present invention provides a solution to the aforementioned limitation of filter-based shock advisory algorithms by detecting asystole rhythms through harnessing information extracted from both a CC-filtered ECG waveform and a recorded CC-corrupted ECG waveform. The result is an increase in the specificity of the shock advisory algorithm during CPR for asystole rhythms. In other words, the present invention proposes to reduce the number for false shocks erroneously advised by shock advisory algorithms for asystole rhythms.

Additionally, in view of a capability of detecting asystole during chest compression, the present invention can assist a user with selecting the correct treatment for a cardiac arrest patient. For example, without the need of pausing CPR for a reliable rhythm analysis, the user can immediately decide if she/he needs to continue chest compression or resort to drug intervention or therapeutic hypothermia based on the asystole detection.

One form of the present invention is a patient monitoring device employing an ECG monitor and a controller. In operation, the ECG monitor monitors a corrupted ECG waveform of a heart of a patient and the controller classifies the corrupted ECG waveform as one of a non-shockable rhythm or a potentially shockable rhythm. Specifically, the controller classifies the corrupted ECG waveform as the non-shockable rhythm responsive to a detection by the controller of a presence of an asystole rhythm within the corrupted ECG waveform. Conversely, the controller classifies the corrupted ECG waveform as the potentially shockable rhythm responsive to a detection by the controller of an absence of the asystole rhythm within the corrupted ECG waveform. The controller can classify the corrupted ECG waveform as the potentially shockable rhythm responsive to an indetermination by the controller as to the presence or the absence of the asystole rhythm within the corrupted ECG waveform. The patient monitoring device according to this form of the present invention can be an AED, ALS defibrillator (or ALS defibrillator/monitor), patient monitor and/or other medical devices having patient monitoring and/or defibrillation functionality.

The foregoing form and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

In a clean ECG waveform (e.g., without any CC artifact), an asystole rhythm shows as almost a flat line, which indicates a state of no or low cardiac electrical activity in the patient's heart. During a chest compression, the asystole rhythm of the ECG waveform is dominated by either the CC artifact ("CC-corrupted ECG waveform") or any filtering residual if the CC artifact is filtered ("CC-filtered ECG waveform"). However, the present invention is premised on a discovery of several signal features preserved in both the CC-corrupted ECG waveform and the CC-filtered ECG waveform that may distinguish a an asystole rhythm from other cardiac rhythms even during chest compression as exemplarily described herein in connection with FIG. 2.

One example of the preserved signal features is an amplitude spectrum area ("AMSA"), which measures the area under the curve from an amplitude frequency spectrum over a certain frequency range. Another example of the preserved signal features is a power of a first difference of ECG (dPower), which measures a temporal smoothness (i.e., slope) of the ECG waveform over a range of one ECG segment.

Generally, the present invention extracts a set of preserved signal features from both a time domain and a frequency domain for a segment of the ECG waveform and the extracted signal features are analyzed to separate and distinguish any asystole rhythm from other cardiac rhythms. More particularly, the set of preserved signal features is extracted from the raw ECG waveform corrupted by the CC artifact as exemplarily described herein in connection with FIG. 4. Alternatively or concurrently, the set of preserved features can be extracted from a processed ECG waveform (e.g., reconstructed and/or filtered). For filtering purposes of the ECG waveform, the present invention proposes any suitable technique as known in the art. For example, a reference signal-based CC filtering and a blind source separation as exemplarily described herein for AMSA and dPower in connection with FIGS. 5 and 6. After extraction, various parameters of the signal features are then analyzed in combination to separate and distinguish any asystole rhythm from other cardiac rhythms. For example, a multi-stage thresholding and a decision tree can be executed to separate and distinguish any asystole rhythm from other cardiac rhythms as exemplarily described herein for AMSA and dPower in connection with FIG. 7.

To facilitate an understanding of the present invention, exemplary embodiments of a cardiac therapy system of the present invention in the form of an automated external defibrillator of the present invention will be provided herein in connection with the description of FIGS. 1-7. While the exemplary embodiments are described in the context of the preserved signal features of a CC-corrupted ECG waveform being ASMA and dPower, those having ordinary skill in the art will appreciate how to apply the principles of the present invention to other preserved signal features of a CC-corrupted ECG waveform. Additionally, while the exemplary embodiments are described in the context of supporting a decision by a shock advisory algorithm with a likelihood estimate of an asystole rhythm to potentially improve upon the CPR quality of the shock advisory algorithm, those having ordinary skill in the art will appreciate how to apply the principles of the present invention for the support of other ECG-based therapy/treatment techniques.

Also, for purposes of the description of the present invention, the terms "ECG waveform", "cardiac rhythm", "shockable rhythm", "non-shockable rhythm", "asystole rhythm", "advisory", "advisor", "electrode pad/paddle", "compression pad" "controller", "ECG monitor", "shock source", "signal conditioner", "feature extractor" and "rhythm classifier" as well as synonymous and related terms are to be broadly interpreted as known in the art of the present invention. Additionally, as generally known in the art, an advanced life support ("ALS") defibrillator/monitor can be synonymously referred to as an advanced life support ("ALS") defibrillator. Further, an ALS defibrillator/monitor (or ALS defibrillator) can include functionality of an Automatic External Defibrillator ("AED") and be operable as an AED in, e.g., an "AED mode".

Figure 1:
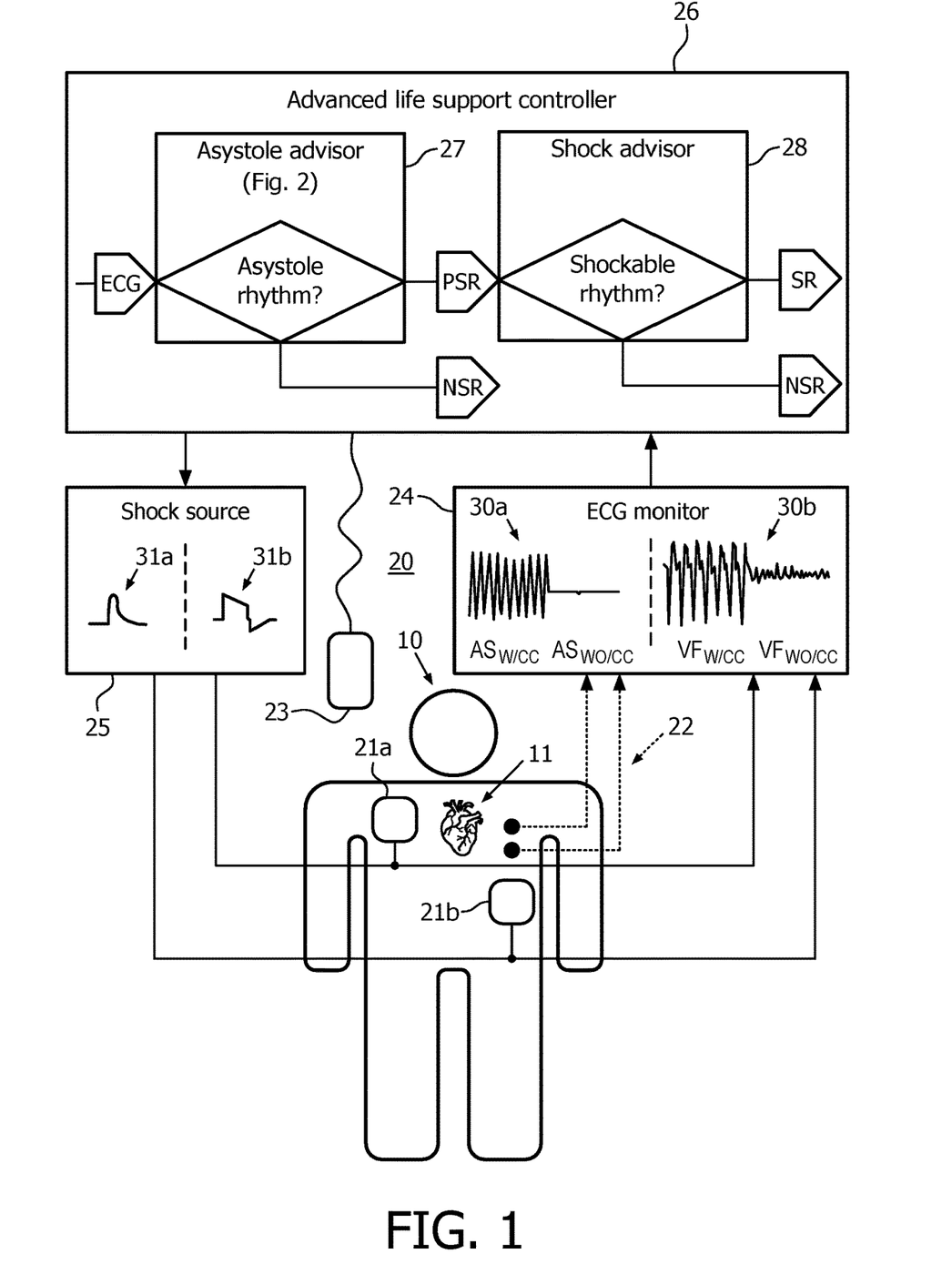
FIG. 1 illustrates an exemplary embodiment of a cardiac therapy system in accordance with the present invention.

Referring to FIG. 1, an advanced life support defibrillator 20 of the present invention employs a pair of electrode pads/paddles 21a and 21b (collectively hereafter as electrode pad/paddles 21), optional ECG leads 22, an optional compression pad 23, an ECG monitor 24 (internal or external), and a shock source 25, and an advanced life support ("ALS") controller 26. Alternatively, an advanced life support monitor of the present invention employs components 21-24 and 26, and omits shock source 25.

Electrode pads/paddles 21 are structurally configured as known in the art to be conductively applied to a patient 10 in an anterior-apex arrangement as shown in FIG. 1 or in an anterior-posterior arrangement (not shown). Electrode pads/paddles 21 conduct a defibrillation shock from shock source 25 to a heart 11 of patient 10 as controlled by controller 26, and conduct electrical activity of heart 11 of patient 10 to ECG monitor 24. Alternatively or concurrently, ECG leads 22 as known in the art may be connected to patient 10 to conduct the electrical activity ofheart 11 of patient 10 to ECG monitor 24.

Compression pad 23 is structurally configured as known in the art to be applied to a chest of patient 10 relative to heart 11 for purposes of providing feedback to controller 26 as shown with the feedback being indicative of a force and/or a rate of a compression motion being applied via compression pad 23 to the chest of patient 10.

ECG monitor 24 is structurally configured as known in the art to measure an ECG waveform 30 of heart 11 of patient 10. Of importance is chest compression corruption of ECG waveform 30 will occur via use of compression pad 23. As shown in FIG. 1, an example is a corrupted ECG waveform 30a having a chest compression ("CC") corruption of an asystole rhythm ("AR"), a non-shockable rhythm. Another example of is a corrupted ECG waveform 30b indicating patient 10 having a chest compression ("CC") corruption of a ventricular fibrillation ("VF"), a shockable rhythm.

In one exemplary embodiment, ECG monitor 24 employs a digital signal processor (not shown) for streaming ECG waveform data to controller 26.

Shock source 25 is structurally configured as known in the art to store electric energy for delivery of a defibrillation shock 31 via electrode pads/paddles 21 to heart 11 of patient 10 as controlled by controller 26. In practice, defibrillation shock 31 can have any waveform as known in the art. Examples of such waveforms include, but are not limited to, a monophasic sinusoidal waveform (positive sine wave) 31a and a biphasic truncated waveform 31b as shown in FIG. 1.

In one exemplary embodiment, shock source 25 employs a high voltage capacitor bank (not shown) for storing a high voltage via a high voltage charger and a power supply upon a pressing of a charge button. Shock source 25 further employs a switching/isolation circuit (not shown) for selectively applying a specific waveform of an electric energy charge from the high voltage capacitor bank to electrode pads/paddles 21 as controlled by controller 26.

Controller 26 is structurally configured with hardware, software, firmware and/or circuitry as known in the art, responsive to corrupted ECG waveform 30 from ECG monitor 24, to control shock source 25 in delivering defibrillation shock 31 via electrode pads/paddles 21 to heart 11 of patient 10 in accordance with one or more shock therapies (e.g, synchronized cardioversion). To this end, the present invention incorporates an asystole advisor 27 and a shock advisor 28 within controller 26 for deciding whether or not to advise a defibrillation of heart 11 of patient 10 based on a detection or a failure to detect an asystole rhythm within corrupted ECG waveform 30. As will be further explained herein, asystole advisor 27 improves upon the accuracy of shock advisor 27 by serving as a pre-processing stage of corrupted ECG waveform 30.

Specifically, as shown in FIG. 1, asystole advisor 27 inputs and processes corrupted ECG waveform 30 for detection of any asystole rhythm within corrupted ECG waveform 30 under the principles of the present invention as will be further described herein in connection with FIGS. 2-8. If asystole advisor 27 detects a presence of an asystole rhythm within corrupted ECG waveform 30, then asystole advisor 27 classifies corrupted ECG waveform 30 as non-shockable rhythm ("NSR"). Otherwise, if asystole advisor 27 detects an absence of an asystole rhythm within corrupted ECG waveform 30 or is indeterminate as to a presence or an absence of an asystole rhythm within corrupted ECG waveform 30, then asystole advisor 27 classifies corrupted ECG waveform 30 as a potentially shockable rhythm ("PSR") and streams corrupted ECG waveform 30 to shock advisor 28 for processing as known in the art to thereby classify the corrupted ECG waveform 30 as shockable rhythm ("SR") or a non-shockable rhythm ("NSR").

Alternatively, for a patient monitor according to the present invention, shock advisor 28 is omitted and asystole advisor 27 can be independently operated for facilitating a clinical decision if chest compression should be continued or halted based on the rhythm classification of corrupted ECG waveform 30 by asystole advisor 27. For this embodiment, one set of outputs for asystole advisor 27 can be "Asystole", "Likely Asystole" and "Not Asystole" whereby the clinician could make an appropriate decision as to whether or not to continue chest compression. Another set of outputs for asystole advisor 27 can be "Non-Shockable Rhythm" when detecting any asystole rhythm within corrupted ECG waveform 30 or "Potentially Shockable Rhythm" when failing to detect any asystole rhythm within corrupted ECG waveform 30.

Figure 2:
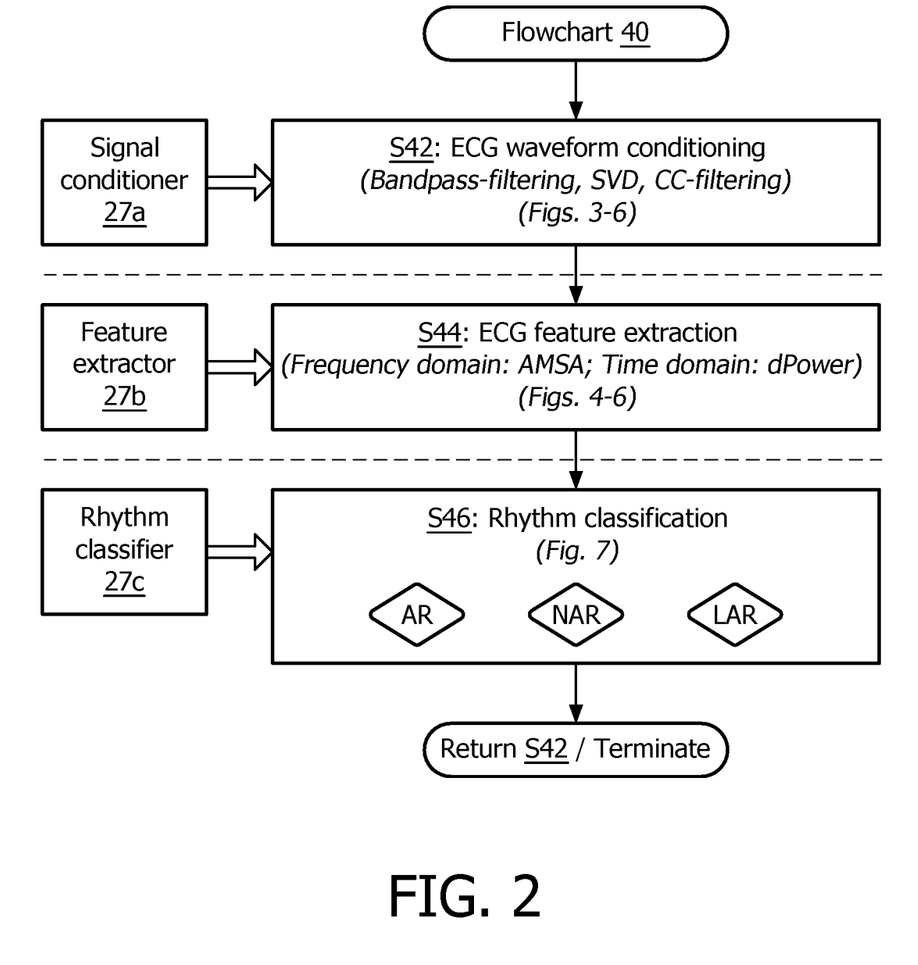
FIG. 2 illustrates a flowchart representative of an exemplary embodiment of an asystole detection method in accordance with the present invention.

Referring to FIG. 2, in detecting any asystole rhythm within corrupted ECG waveform 30, asystole advisor 27 can employ a signal conditional 27a, a feature extractor 27b and a rhythm classifier 27c for executing a flowchart 40 representative of an asystole detection method of the present invention, particularly for a CC-corruption of corrupted ECG waveform 30.

Specifically, signal conditioner 27a implements known signal condition technique(s) during a stage S42 of flowchart 40 for conditioning corrupted ECG waveform 30 in multiple forms whereby feature extractor 27b implements known feature extraction technique(s) during a stage S44 of flowchart 40 for extracting a frequency domain feature and/or a time domain feature from the multiple forms of the conditioned corrupted ECG waveform 30.

Examples of known signal condition technique(s) include, but are not limited to, sampling, bandpass filtering, singular value decomposition ("SVD"), CC-artifact filtering (e.g., SB filtering) and a signal reconstruction.

An example of a frequency domain feature of the conditioned corrupted ECG waveform 30 includes, but is not limited to, an amplitude spectrum area ("ASMA") of corrupted ECG waveform 30, and an example of a time domain feature of the conditioned corrupted ECG waveform 30 includes, but is not limited to, is-a dPower of corrupted ECG waveform 30.

Figure 3:
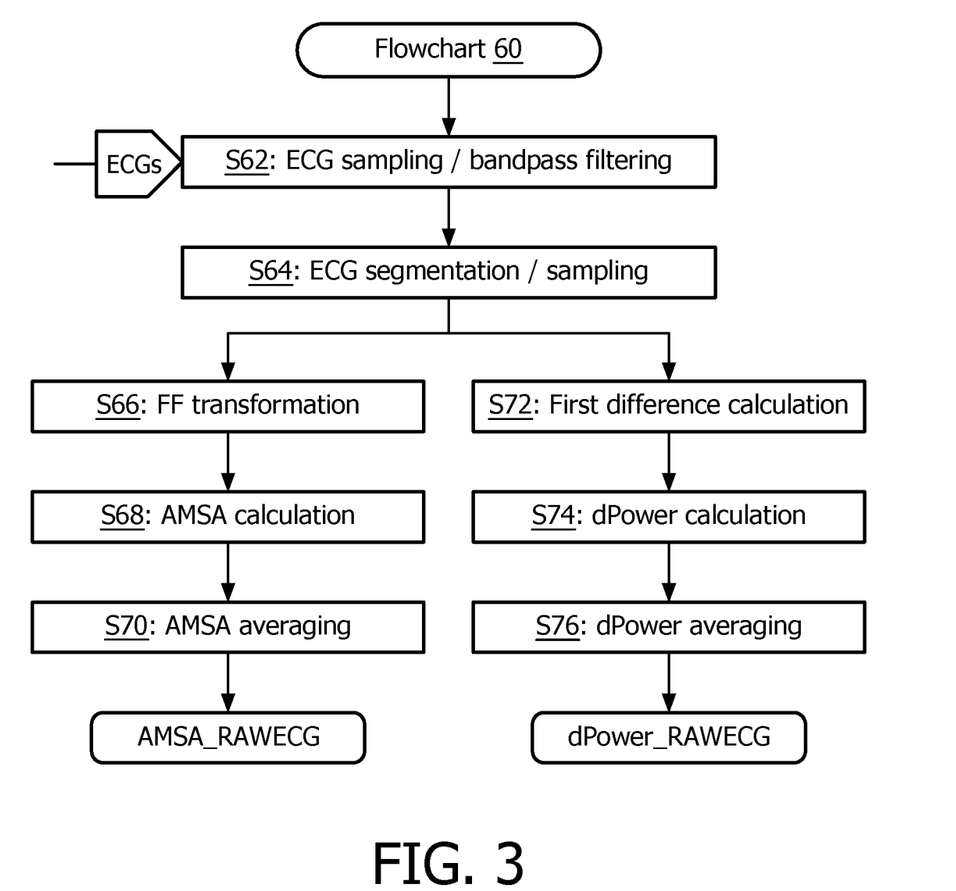
FIG. 3 illustrates a flowchart representative of an exemplary embodiment of a raw ECG extraction method in accordance with the present invention.
Figure 4:
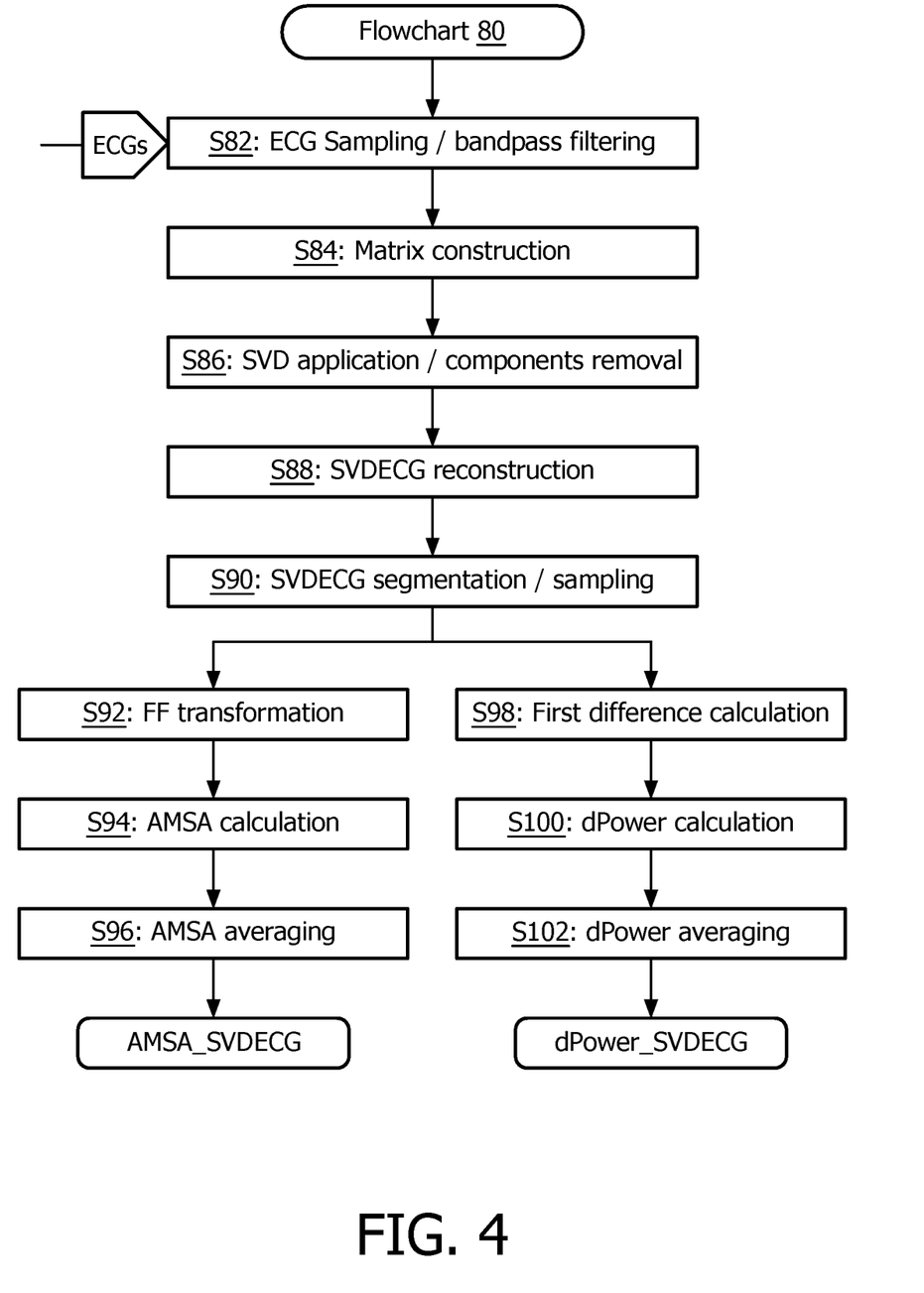
FIG. 4 illustrates a flowchart representative of an exemplary embodiment of a singular value decomposition extraction method in accordance with the present invention.
Figure 5:
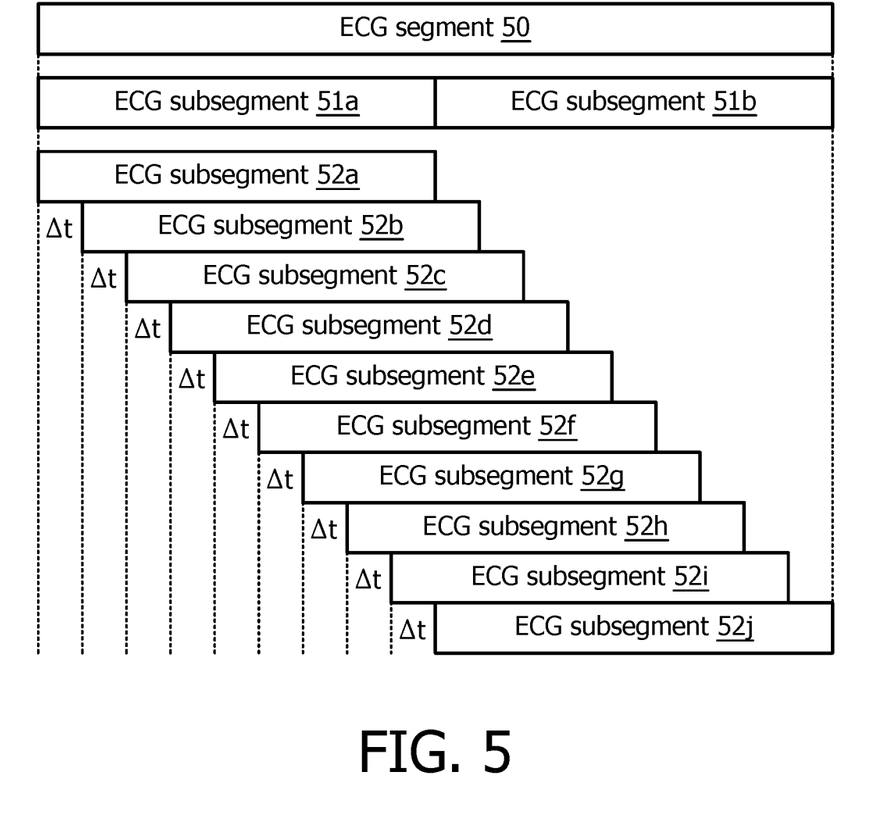
FIG. 5 illustrates an exemplary subsegmentation/matrix construction of an ECG waveform in accordance with the present invention.
Figure 6:
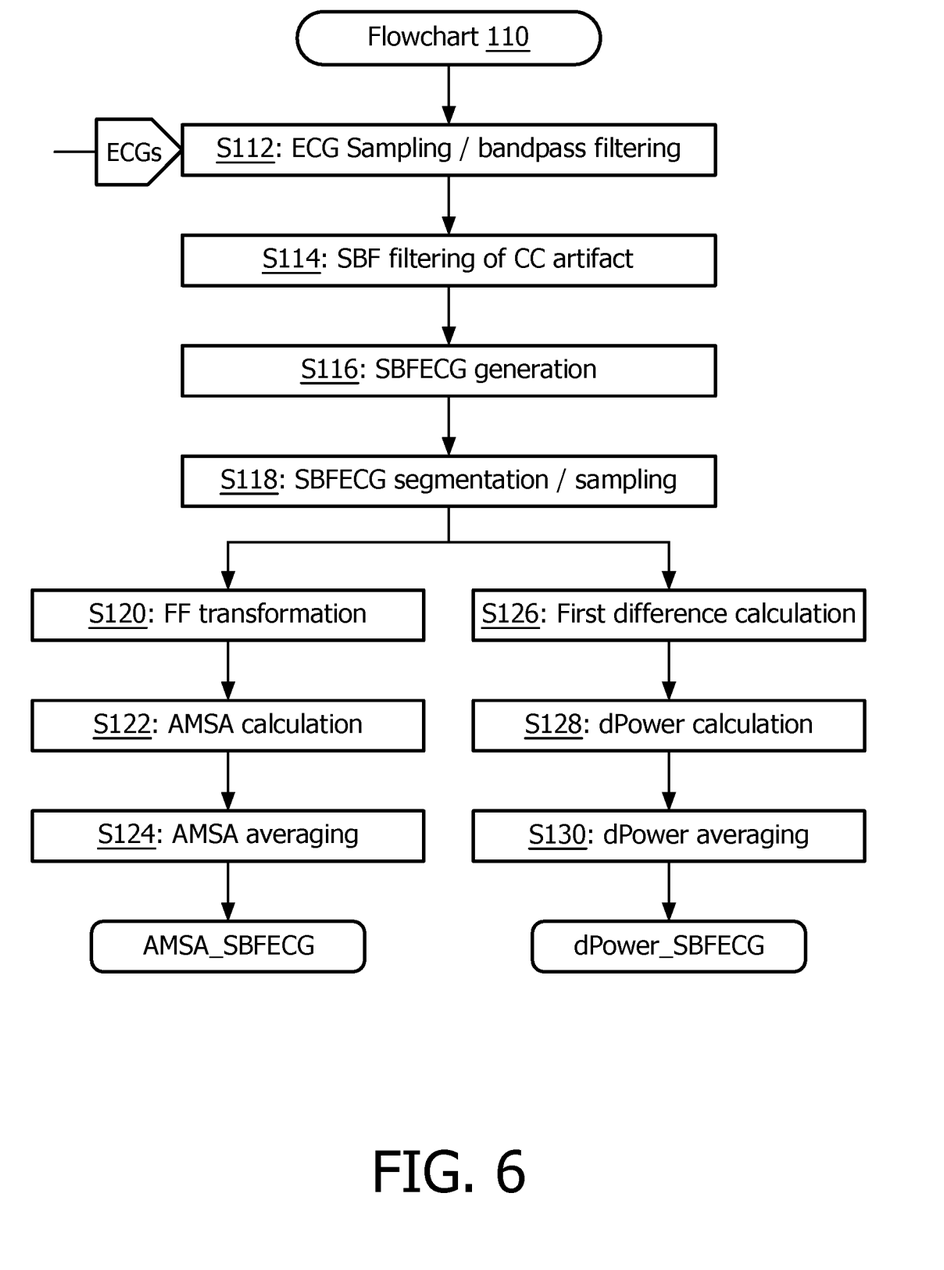
FIG. 6 illustrates a flowchart representative of an exemplary embodiment of a SB filter extraction method in accordance with the present invention.

To facilitate a further understanding of stages S42 and S44 of flowchart 40, a description will now be provided herein of (1) a flowchart 60 representative of a raw ECG extraction method of the present invention as shown in FIG. 3, (2) a flowchart 80 representative of a SVD extraction method of the present invention as shown in FIG. 4, (3) a ECG subsegmentation/matrix construction in accordance with the present invention as shown in FIG. 5, and (4) a flowchart 110 representative of a SB filtering extraction method of the present invention as shown in FIG. 6.

Referring to FIG. 3, a stage S62 of flowchart 60 encompasses signal conditioner 27a sampling an ECG segment 50 (FIG. 5) of corrupted ECG waveform 30 (e.g., a 4.5 second segment @200 samples/sec) and bandpass filtering ECG segment 50 (e.g., 1 Hz-30 Hz cutoff frequencies). A stage S64 of flowchart 60 encompasses signal conditioner 27a further segmenting ECG segment 50 into two (2) equal subsegments 51a and 51b (FIG. 5) that are sampled by feature extractor 27b (e.g., a 2.25 second segments @200 samples/sec).

To distinguish any asystole rhythm from shockable rhythms, stages S66-S70 of flowchart 60 extract an AMSA feature from the ECG subsegments 51a and 51b of stage S64, and stages S72-S76 of flowchart 60 extract a dPower feature from the ECG subsegments 51a and 51b of stage S64.

Specifically, AMSA measures an area under a curve from an amplitude frequency spectrum over a certain frequency range. To extract the ASMA from each ECG subsegment 51, feature extractor 27b executes a Fast Fourier Transform (FFT) during stage S66 on each ECG subsegment 51 to thereby obtain a frequency spectrum of each ECG subsegment 51, and calculates the AMSA for each ECG subsegment 51 in accordance with the AMSA=×$F_i$, where $A_i$ is the amplitude at the $i^{th}$ frequency $F_i$ over the frequency range between 1 Hz-30 Hz.

Stage S70 encompasses feature extractor 27b averaging the ASMA for each ECG subsegment 51 to yield a raw frequency variable AMSA_RAWECG.

Concurrently, feature extractor 27b measures a first difference of each ECG subsegment 51 during stage S72 and calculates the dPower of the measured first difference of each ECG subsegment 51 during stage S74. Stage S76 encompasses feature extractor 27b averaging the dPower of each ECG subsegment 51 to yield a raw frequency variable dPOWER_RAWECG.

Referring to FIG. 4, a stage S82 of flowchart 80 encompasses signal conditioner 27a sampling and bandpass filtering a ECG segment 50 (FIG. 5) of corrupted ECG waveform 30 as previously described herein. A stage S84 of flowchart 80 encompasses signal conditioner 27a constructing an ECG matrix 52 of subsegments 52a-52j having an equal time window (e.g., 2.25 seconds) and each row being shifted by a step window Δt (e.g., 0.25 seconds), and a stage S86 of flowchart 80 encompasses signal conditioner 27a applying a singular value decomposition (SVD) on ECG matrix 52a-52j to decompose ECG matrix 52a-52j into spatial components and temporal components. Spectral analysis on the temporal components of ECG matrix will typically show that the first several major components are dominated by the CC artifact (e.g., first 3 temporal components). These several major temporal components are removed, and the remaining components are re-combined by signal conditioner 27a during a stage S88 of flowchart 80 to build a reconstructed ECG matrix 52a-52j, which is re-organized to become a reconstructed ECG segment SVDECG representative of ECG segment 50 being processed via a SVD-based method of blind source separation called principal component analysis ("PCA"). One advantage of reconstructed ECG segment SVDECG is that no additional reference signal is needed to remove any CC artifact from ECG segment 50.

A stage S90 of flowchart 80 encompasses signal conditioner 27a further segmenting reconstructed ECG segment SVDECG into two (2) equal subsegments that are sampled by feature extractor 27b (e.g., a 2.25 second segments @200 samples/sec).

To distinguish any asystole rhythm from shockable rhythms, during stages S92-S96 of flowchart 80, feature extractor 27b extracts an AMSA feature from the subsegments of reconstructed ECG segment SVDECG of stage S90 to yield a SVD frequency variable AMSA_SVDECG similar to the extraction of the AMSA from the raw ECG segment 50 as previously described herein.

Concurrently, during stages S98-S102 of flowchart 90, feature extractor 27b extracts a dPower feature from the subsegments of reconstructed ECG segment SVDECG of stage S90 to yield a SVD time variable dPOWER_SVDECG similar to the extraction of the dPower from the raw ECG segment 50 as previously described herein.

Referring to FIG. 6, a stage S112 of flowchart 110 encompasses signal conditioner 27a sampling and bandpass filtering an ECG segment 50 (FIG. 5) of corrupted ECG waveform 30 as previously described herein. A stage S114 of flowchart 110 encompasses signal conditioner 27a applying a SB filter to ECG segment 50 to remove any CC-artifact with ECG segment 50, and a stage S116 of flowchart 110 encompasses signal conditioner 27a generating a filtered ECG segment SBEFCG.

A stage S118 of flowchart 110 encompasses signal conditioner 27a further segmenting filtered ECG segment SBEFCG into two (2) equal subsegments that are sampled by feature extractor 27b (e.g., a 2.25 second segments @200 samples/sec).

To distinguish any asystole rhythm from shockable rhythms, during stages S120-S124 of flowchart 110, feature extractor 27b extracts an AMSA feature from the subsegments of filtered ECG segment SBEFCG of stage S118 to yield a SBF frequency variable AMSA_SBFECG similar to the extraction of the AMSA from the raw ECG segment 50 as previously described herein.

Concurrently, during stages S126-S130 of flowchart 110, feature extractor 27b extracts a dPower feature from the subsegments filtered ECG segment SBEFCG of stage S118 to yield a SBF time variable dPOWER_SBFECG similar to the extraction of the dPower from the raw ECG segment 50 as previously described herein.

Referring back to FIG. 2, rhythm classifier 27c processes the aforementioned extracted AMSA/dPower variables (FIGS. 3, 4 & 6) through a multi-stage thresholding/decision tree during a stage S46 of flowchart 40 to yield a classification of corrupted ECG waveform 30 (FIG. 1) as either an asystole rhythm ("AR"), a not-asystole rhythm ("NAR"), and a likely-asystole rhythm ("LAR"). More particularly, asystole rhythm AR means rhythm classifier 27c is certain that analyzed corrupted ECG waveform 30 has an asystole rhythm. Conversely, not-asystole rhythm NAR means rhythm classifier 27c is certain that analyzed corrupted ECG waveform 30 has a not-asystole rhythm. Of unique significance is likely-asystole rhythm LAR means rhythm classifier 27c thinks that the analyzed corrupted ECG waveform 30 can have an asystole rhythm, but further analysis is needed to confirm (e.g., by pausing CC and analyzing a clean ECG).

Figure 7:
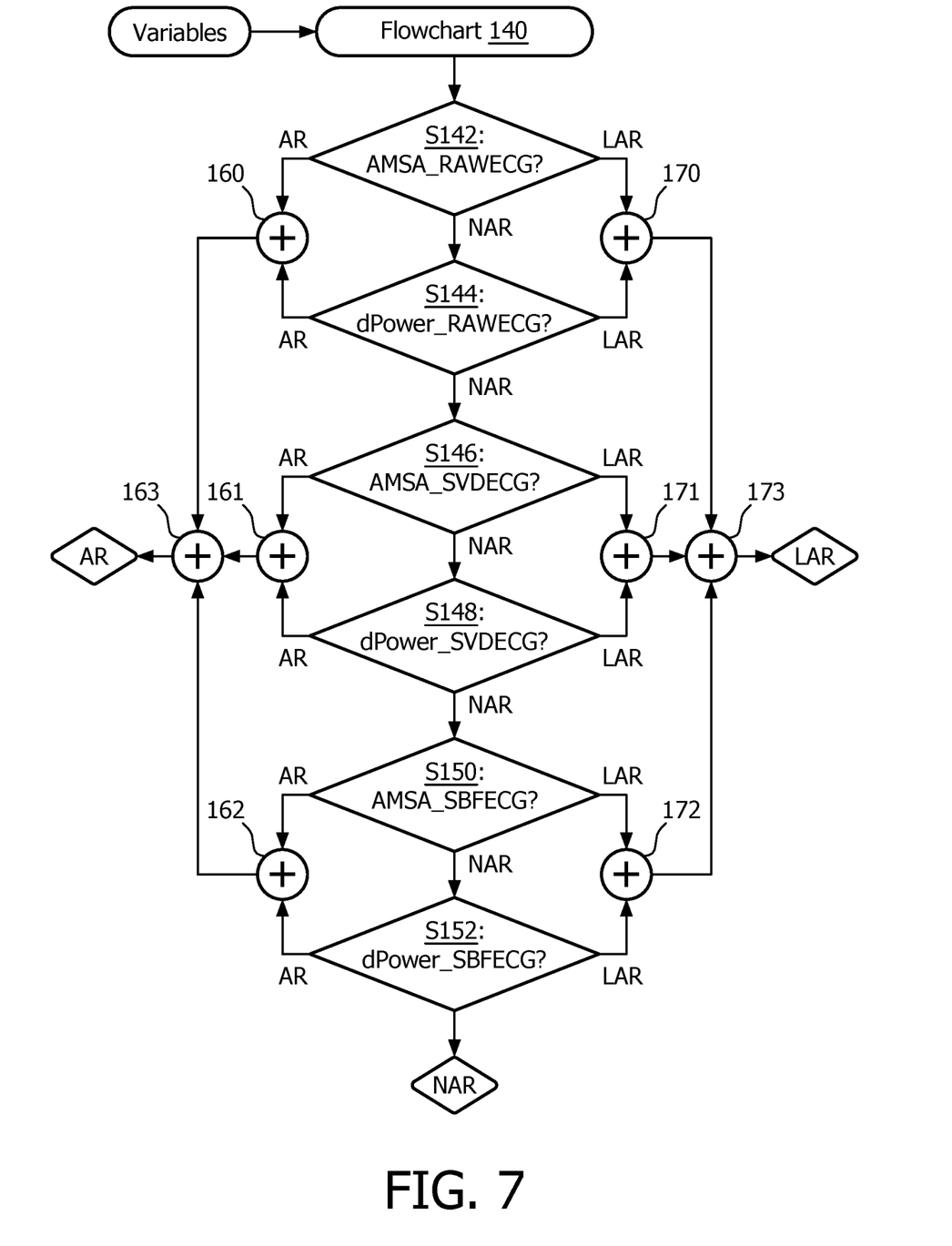
FIG. 7 illustrates a flowchart representative of an exemplary embodiment of rhythm classification method in accordance with the present invention.

To facilitate a further understanding stage S46 of flowchart 40, a description will now be provided herein of a flowchart 140 representative of a rhythm classification method of the present invention as shown in FIG. 7. Referring to FIG. 7, the multi-stage thresholding/decision tree implemented by flowchart 140 involves flowing through stages S142-S152 of flowchart 140 until such time rhythm classifier 27c classifies the ECG waveform as an asystole rhythm AR, a not-asystole rhythm NAR, and a likely-asystole rhythm LAR.

Specifically, flowchart 140 inputs variables comparing raw frequency variable AMSA_RAWECG (FIG. 3), raw time variable dPOWER_RAWECG (FIG. 3), SVD frequency variable AMSA_SVDECG (FIG. 4), SVD time variable dPOWER_SVDECG (FIG. 4), SBF frequency variable AMSA_SBFECG (FIG. 6) and SBF time variable dPOWER_SBFECG (FIG. 6).

In practice, for ventricular fibrillation ("VF"), raw frequency variable AMSA_RAWECG will typically be greater than 18.59, raw time variable dPOWER_RAWECG will typically be greater than 0.047, SVD frequency variable AMSA_SVDECG will typically be greater than 13.57, SVD time variable dPOWER_SVDECG will typically be greater than 0.030, SBF frequency variable AMSA_SBFECG will typically be greater than 12.93 and SBF time variable dPOWER_SBFECG will typically be greater than 0.033.

Stage S142 of flowchart 140 encompasses rhythm classifier 27c comparing raw frequency variable AMSA_RAWECG to an asystole detection threshold (e.g., 18.59) and to a not-asystole detection threshold (e.g., 47.43). If theraw frequency variable AMSA_RAWECG is less than the asystole detection threshold, then rhythm classifier 27c proceeds through OR circuits 160 and 163 to yield a classification of corrupted ECG waveform 30 as asystole rhythm AR.

If theraw frequency variable AMSA_RAWECG is greater than the asystole detection threshold and equal to or less than the not-asystole detection threshold, then rhythm classifier 27c proceeds through OR circuits 170 and 173 to yield a classification of corrupted ECG waveform 30 as likely-asystole rhythm LAR. Otherwise, with raw frequency variable AMSA_RAWECG being greater than the not-asystole detection threshold, rhythm classifier 27c proceeds to stage S144 to test raw time variable dPOWER_RAWECG (FIG. 3).

Stage S144 of flowchart 140 encompasses rhythm classifier 27c comparing raw time variable dPOWER_RAWECG to an asystole detection threshold (e.g., 0.047) and to a not-asystole detection threshold (e.g., 0.447). If the raw time variable dPOWER_RAWECG is less than the asystole detection threshold, then rhythm classifier 27c proceeds through OR circuits 160 and 163 to yield a classification of corrupted ECG waveform 30 as asystole rhythm AR.

If the –raw time variable dPOWER_RAWECG is greater than the asystole detection threshold and equal to or less than the not-asystole detection threshold, then rhythm classifier 27c proceeds through OR circuits 170 and 173 to yield a classification of corrupted ECG waveform 30 as likely-asystole rhythm LAR. Otherwise, with raw time variable dPOWER_RAWECG being greater than the not-asystole detection threshold, rhythm classifier 27c proceeds to stage S146 to test SVD frequency variable AMSA_SVDECG (FIG. 4).

Stage S146 of flowchart 140 encompasses rhythm classifier 27c comparing SVD frequency variable AMSA_SVDECG to an asystole detection threshold (e.g., 13.57) and to a not-asystole detection threshold (e.g., 28.99). If the –SVD frequency variable AMSA_SVDECG is less than the asystole detection threshold, then rhythm classifier 27c proceeds through OR circuits 161 and 163 to yield a classification of corrupted ECG waveform 30 as asystole rhythm AR.

If the –SVD frequency variable AMSA_SVDECG is greater than the asystole detection threshold and equal to or less than the not-asystole detection threshold, then rhythm classifier 27c proceeds through OR circuits 171 and 173 to yield a classification of corrupted ECG waveform 30 as likely-asystole rhythm LAR. Otherwise, with SVD frequency variable AMSA_SVDECG being greater than the not-asystole detection threshold, rhythm classifier 27c proceeds to stage S148 to test SVD time variable dPOWER_SVDECG (FIG. 4).

Stage S148 of flowchart 140 encompasses rhythm classifier 27c comparing SVD time variable dPOWER_SVDECG to an asystole detection threshold (e.g., 0.030) and to a not-asystole detection threshold (e.g., 0.182). If the SVD time variable dPOWER_SVDECG is less than the asystole detection threshold, then rhythm classifier 27c proceeds through OR circuits 161 and 163 to yield a classification of corrupted ECG waveform 30 as asystole rhythm AR.

If the SVD time variable dPOWER_SVDECG is greater than the asystole detection threshold and equal to or less than the not-asystole detection threshold, then rhythm classifier 27c proceeds through OR circuits 171 and 173 to yield a classification of corrupted ECG waveform 30 as likely-asystole rhythm LAR. Otherwise, with SVD time variable dPOWER_SVDECG being greater than the not-asystole detection threshold, rhythm classifier 27c proceeds to stage S150 to test SBF frequency variable AMSA_SBFECG (FIG. 6).

Stage S150 of flowchart 140 encompasses rhythm classifier 27c comparing SBF frequency variable AMSA_SBFECG to an asystole detection threshold (e.g., 12.93) and to a not-asystole detection threshold (e.g., 29.99). If the SBF frequency variable AMSA_SBFECG is less than the asystole detection threshold, then rhythm classifier 27c proceeds through OR circuits 162 and 163 to yield a classification of corrupted ECG waveform 30 as asystole rhythm AR.

If the –SBF frequency variable AMSA_SBFECG is greater than the asystole detection threshold and equal to or less than the not-asystole detection threshold, then rhythm classifier 27c proceeds through OR circuits 172 and 173 to yield a classification of corrupted ECG waveform 30 as likely-asystole rhythm LAR. Otherwise, with SBF frequency variable AMSA_SBFECG being greater than the not-asystole detection threshold, rhythm classifier 27c proceeds to stage S152 to test SBF time variable dPOWER_SBFECG (FIG. 4).

Stage S152 of flowchart 140 encompasses rhythm classifier 27c comparing SBF time variable dPOWER_SBFECG to an asystole detection threshold (e.g., 0.033) and to a not-asystole detection threshold (e.g., 0.227). If the SBF time variable dPOWER_SBFECG is less than the asystole detection threshold, then rhythm classifier 27c proceeds through OR circuits 162 and 163 to yield a classification of corrupted ECG waveform 30 as asystole rhythm AR.

If the SBF time variable dPOWER_SBFECG is greater than the asystole detection threshold and equal to or less than the not-asystole detection threshold, then rhythm classifier 27c proceeds through OR circuits 172 and 173 to yield a classification of corrupted ECG waveform 30 as likely-asystole rhythm LAR. Otherwise, with SBF time variable dPOWER_SBFECG being greater than the not-asystole detection threshold, rhythm classifier 27c proceeds to stage S152 to yield a classification of corrupted ECG waveform 30 as not-asystole rhythm NAR.

In an alternative embodiment of flowchart 140, OR circuits 170-173 are replaced by AND circuits, and a LAR classification for each stage is feed to a corresponding AND circuit and also triggers stages S142-S150 to proceed to the next stage. The exception would be stage S152 whereby a LAR classification is only feed to the corresponding AND circuit. The result of this embodiment, assuming each stage failed to classify an AR, is stage S152 will either (1) output a LAR classification based on all stages S142-S152 reaching a LAR classification or (2) output a NA classification because of a failure of one of the stages S142-S152 to classify a LAR.

In another alternative embodiment of flowchart 140, OR circuit 173 is replaced by AND circuits, and a LAR classification for each stage is feed to a corresponding OR circuit and also triggers stages S142-S150 to proceed to the next stage. The exception would be stage S152 whereby a LAR classification is only feed to the corresponding OR circuit. The result of this embodiment, assuming each stage failed to classify an AR, is stage S152 will either (1) output a LAR classification based on each stage pairing S142/S144, S146/S148 and S150/S152 reaching a LAR classification or (2) output a NA classification because of a failure of one of the stage pairings S142/S144, S146/S148 and S150/S152 to classify a LAR.

Referring back to FIG. 2, modules 27a-27c loop through stages S142-S146 as needed until such time the monitoring of corrupted ECG waveform 30 is terminated.

Figure 8A:
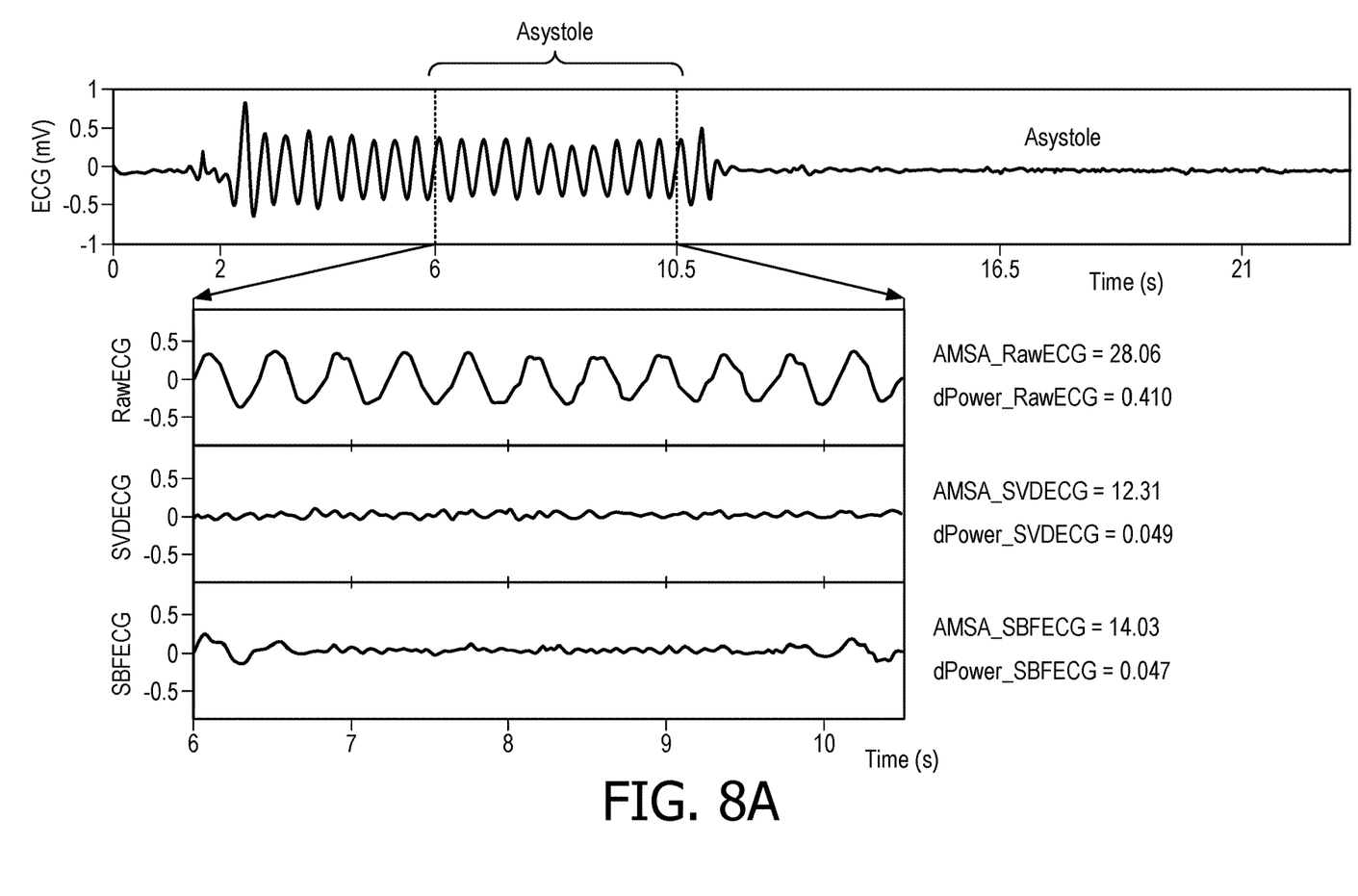
FIGS. 8A-8C illustrate three (3) exemplary examples of an execution of the flowcharts of FIGS. 4-7 on clinical ECG recordings.
Figure 8B:
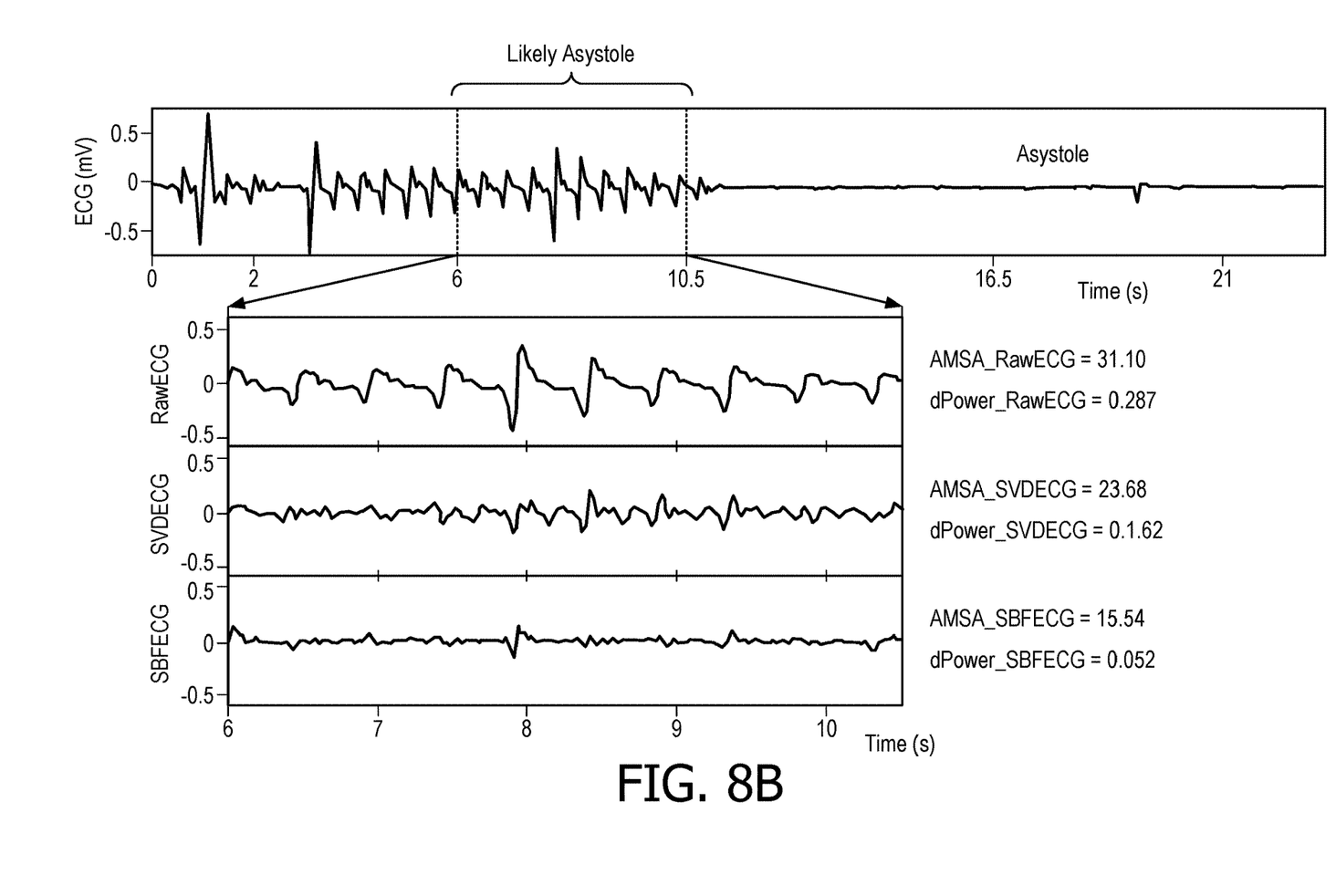
Figure 8C:
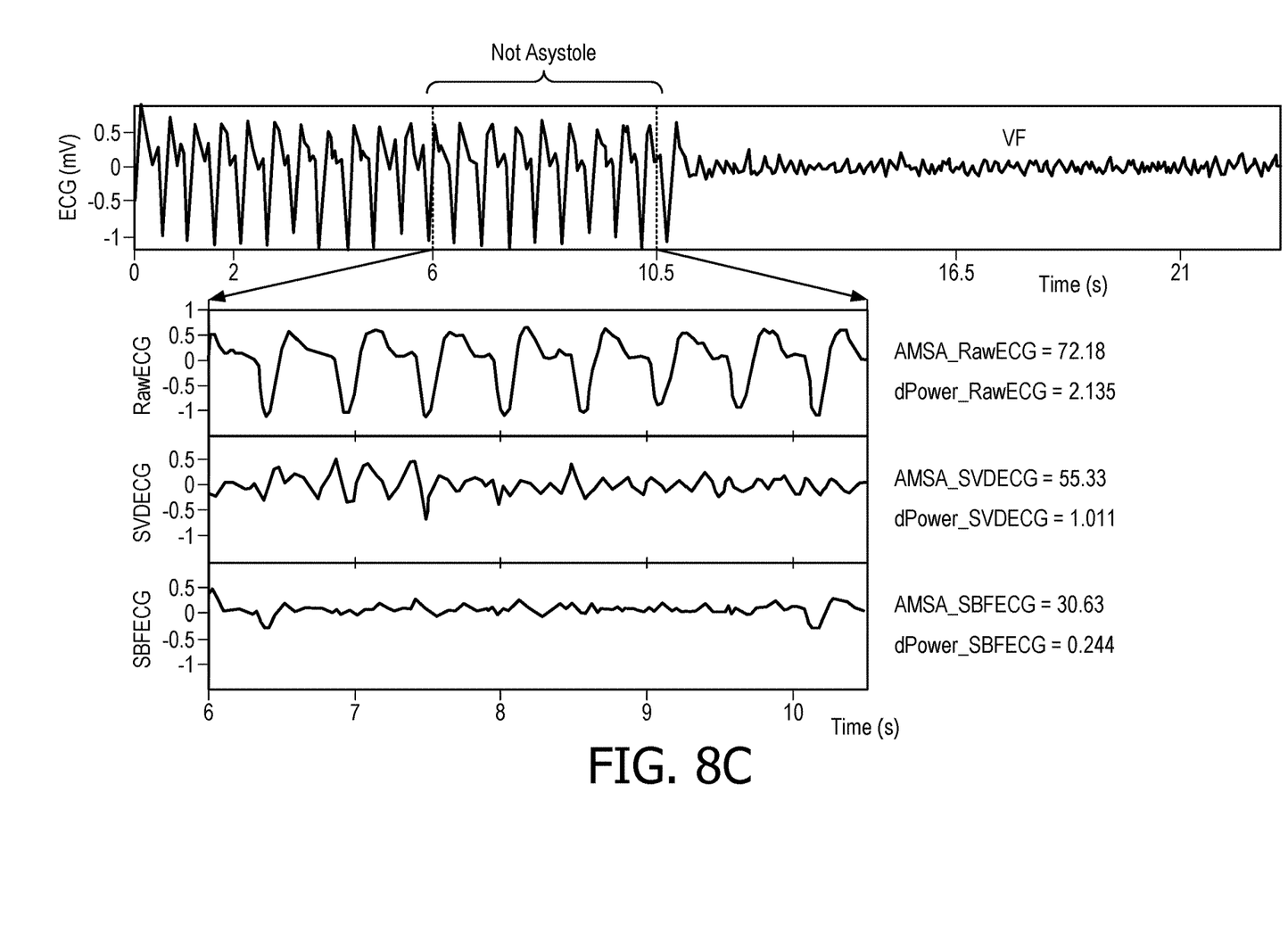

FIGS. 8A-8C shows three (3) examples of running the asystole detection method of the flowcharts of FIGS. 4-7 ("asystole algorithm") on clinical ECG recordings. In all examples, the flowcharts of FIGS. 4-7 are applied on individual fixed-length ECG segments to (1) process the ECG signal into RawECG, SVDECG, and SBFECG and (2) generate the classification of the three categories: "Asystole", "Not Asystole", and "Likely Asystole". Each example also compares the output of the shock-advisory method from a commercial shock advisory algorithm applied on the CC-filtered ECG using SBF with the output generated by the asystole algorithm.

FIG. 8A, in general, is an example of the asystole rhythm correctly classified as "Asystole" by the asystole algorithm with the same rhythm being misclassified as shockable by a shock advisory algorithm after filtering the chest compression ("CC") artifact. Specifically, a portion of a clinical ECG recording as shown in FIG. 8A indicates the transition from performing CC to hands-off without performing CC. In the top row of FIG. 8, the left part is ECG with CC artifact and the right part is ECG without CC artifact (hand-off period). The two bars on the ECG signal indicate a 4.5-sec segment used for analysis. A commercial shock advisory algorithm applied on the CC-filtered ECG erroneously identified this ECG segment as shockable. Rows 2-4 of FIG. 8A respectively show RawECG, SVDECG and SBFECG when using the asystole algorithm for the same ECG segment. The output of the asystole algorithm correctly classified this case into category "Asystole", which is considered a non-shockable rhythm. This example suggests that the present invention could potentially help the shock advisory algorithm in detecting this non-shockable rhythm, and thus improves the performance (specificity) of shock advisory algorithm.

FIG. 8B, in general, is an example of an asystole case classified as "Likely Asystole" by the asystole algorithm. Specifically, the shock advisory algorithm applied on a CC-corrupted ECG segment identified the rhythm as organized (a non-shockable rhythm). Rows 2-4 of FIG. 8B respectively show RawECG, SVDECG and SBFECG when using the asystole algorithm for the same ECG segment, and the output of the asystole algorithm classified this case into the category "Likely Asystole", indicating the asystole algorithm considers this case is possibly asystole, but further analysis is needed. This case also suggests the asystole algorithm could potentially help in making correct decision when combining with other techniques.

FIG. 8C, in general, is an example of a ventricular fibrillation ("VF") case correctly classified as "Not Asystole" by asystole algorithm. Specifically, the ECG recording of FIG. 8C has a VF rhythm (shockable) is illustrated in FIG. 8. The shock advisory algorithm applied on CC-corrupted ECG segment incorrectly identified the rhythm as non-shockable. The shock advisory algorithm applied on ECG after filtering CC artifact improves the performance by correctly identifying the rhythm as shockable. Rows 2-4 of FIG. 8B respectively show RawECG, SVDECG and SBFECG when using the asystole algorithm for the same ECG segment, and the output of the asystole algorithm correctly classifies this case into the category "Not Asystole".

Referring back to FIG. 1, from the preceding description of FIGS. 2-7, those having ordinary skill in the art will appreciate an improvement by asystole advisor 27 in the accuracy of shock advisor 28 by serving as a pre-processing stage of any corrupted ECG waveform 30, or alternatively facilitating a clinical decision if chest compression should be continued (asystole rhythm/likely asystole rhythm) or halted (not-asystole rhythm) based on the rhythm classification of corrupted ECG waveform 30 by asystole advisor 27.

Referring to FIGS. 1-8, those having ordinary skill in the art will appreciate numerous benefits of the present invention including, but not limited to, improving performance of advanced life support devices by detecting any asystole rhythm, a non-shockable rhythm, during CPR of a sudden cardiac arrest patient.

While various embodiments of the present invention have been illustrated and described, it will be understood by those skilled in the art that the embodiments of the present invention as described herein are illustrative, and various changes and modifications can be made and equivalents can be substituted for elements thereof without departing from the true scope of the present invention. In addition, many modifications can be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A patient monitoring device, comprising:
an ECG monitor operable to monitor a corrupted ECG waveform; and
a controller operably connected to the ECG monitor to classify the corrupted ECG waveform as one of a non-shockable asystole rhythm, or a potentially shockable non-asystole rhythm,
wherein the controller is configured to detect a presence or an absence of an asystole rhythm within a segment of the corrupted ECG waveform as indicated by at least one time domain feature and at least one frequency domain feature extracted by the controller from the segment of the corrupted ECG waveform,
wherein the controller is further configured to classify the corrupted ECG waveform as the non-shockable asystole rhythm responsive to a detection by the controller of the presence of the asystole rhythm within the corrupted ECG waveform, and
wherein the controller is further configured to classify the corrupted ECG waveform as the potentially shockable non-asystole rhythm responsive to a detection by the controller of the absence of the asystole rhythm within the corrupted ECG waveform.

2. The patient monitoring device of claim 1, wherein the controller is further configured to classify the corrupted ECG waveform as the potentially shockable non-asystole rhythm responsive to an indetermination by the controller as to the presence or the absence of the asystole rhythm within the corrupted ECG waveform.

3. The patient monitoring device of claim 1, wherein the patient monitoring device is at least one of an automatic external defibrillator or an advanced life support defibrillator.

4. The patient monitoring device of claim 1, wherein the patient monitoring device comprises at least one of an automatic external defibrillator, an advanced life support defibrillator or a patient monitor.

5. The patient monitoring device of claim 1, wherein the controller includes:

a signal conditioner operably connected to the ECG monitor and configured to condition the segment of the corrupted ECG waveform; and a feature extractor operably connected to the signal conditioner and configured to extract the at least one time domain feature and the at least one frequency domain feature from the conditioned segment of the corrupted ECG waveform.

6. The patient monitoring device of claim 5, wherein the signal conditioner removes any artifact from the segment of the ECG waveform.

7. The patient monitoring device of claim 5, wherein the signal conditioner removes a chest compression artifact from segment of the ECG waveform.

8. The patient monitoring device of claim 5, wherein the controller further includes a rhythm classifier operably connected to the feature extractor and configured to detect any indication by the at least one time domain feature and the at least one frequency domain feature of the presence of the asystole rhythm within the conditioned segment of the corrupted ECG waveform.

9. The patient monitoring device of claim 5, wherein the controller further includes a rhythm classifier operably connected to the feature extractor and configured to detect any indication by the at least one time domain feature and the at least one frequency domain feature of the absence of the asystole rhythm within the conditioned segment of the corrupted ECG waveform.

10. The patient monitoring device of claim 5, wherein the controller further includes a rhythm classifier operably connected to the feature extractor and configured to detect any failure by the at least one time domain feature and the at least one frequency domain feature to indicate one of the presence or the absence of the asystole rhythm within the conditioned segment of the corrupted ECG waveform.

11. The patient monitoring device of claim 1, wherein the at least frequency domain feature includes an amplitude spectrum area and the at least one time domain feature includes a first difference power of the corrupted ECG waveform.

12. The patient monitoring device of claim 1, wherein the controller being configured to detect the presence or the absence of the asystole rhythm within the segment of the corrupted ECG waveform as indicated by the at least one frequency domain feature includes the controller configured to:
  extract an amplitude spectrum area based frequency variable from the segment of the corrupted ECG waveform; and
  compare the amplitude spectrum area based frequency variable to at least one of an asystole detection threshold and a not-asystole detection threshold.

13. The patient monitoring device of claim 1, wherein the controller being configured to detect the presence or the absence of the asystole rhythm within the segment of the corrupted ECG waveform as indicated by the at least one time domain feature includes the controller configured to:
  extract a first difference power based time variable from the segment of the corrupted ECG waveform; and
  compare the first difference power based time variable to at least one of an asystole detection threshold and a not-asystole detection threshold.

14. A patient monitoring device controller, comprising:
  a feature extractor configured to extract at least one time domain feature and at least one frequency domain feature from a segment of a corrupted ECG waveform,
  an asystole advisor operably connected to the feature extractor to classify the corrupted ECG waveform as one of a non-shockable asystole rhythm or a potentially shockable non-asystole rhythm based on an extraction by the feature extractor of the at least one time domain feature and at least one frequency domain feature from the segment of the corrupted ECG waveform,
    wherein the asystole advisor is configured to detect a presence or an absence of an asystole rhythm within the segment of the corrupted ECG waveform as indicated by the least one time domain feature and at least one frequency domain feature,
    wherein the asystole advisor is further configured to classify the corrupted ECG waveform as the non-shockable asystole rhythm responsive to a detection by the asystole advisor of the presence of the asystole rhythm within the corrupted ECG waveform, and
    wherein the asystole advisor is further classified to classify the corrupted ECG waveform as the potentially shockable non-asystole rhythm responsive to a detection by the asystole advisor of the absence of the asystole rhythm within the corrupted ECG waveform; and
  a shock advisor operably connected to the asystole advisor to classify the corrupted ECG waveform as either a shockable non-asystole rhythm or a non-shockable non-asystole rhythm responsive to the asystole advisor classifying the corrupted ECG waveform as the potentially shockable non-asystole rhythm.

15. The patient monitoring device controller of claim 14, wherein the asystole advisor classifies the corrupted ECG waveform as the potentially shockable non-asystole rhythm responsive to an indetermination by the asystole advisor as to the presence or the absence of the asystole rhythm within the corrupted ECG waveform.

16. The patient monitoring device controller of claim 14, further comprising:
  a signal conditioner operable to condition the segment of the corrupted ECG waveform; and
  wherein the feature extractor is operably connected to the signal conditioner and configured to extract the at least one time domain feature and at the at least one frequency domain feature from a conditioned segment of the corrupted ECG waveform.

17. The patient monitoring device controller of claim 16, wherein the asystole advisor includes:
  a rhythm classifier operably connected to the feature extractor and configured to:
    (i) detect any indication by at least one of the at least one time domain feature and the at least one frequency domain feature of the presence of the asystole rhythm within the conditioned segment of the corrupted ECG waveform,
    (ii) detect any indication by the at least one of the at least one time domain feature and the at least one frequency domain feature of the absence of the asystole rhythm within the conditioned segment of the corrupted ECG waveform, and
    (iii) detect any failure by the at least one of the at least one time domain feature and the at least one frequency domain feature to indicate one of the presence and the absence of the asystole rhythm within the conditioned segment of the corrupted ECG waveform.

18. The patient monitoring device controller of claim 14, wherein the at least frequency domain feature includes an amplitude spectrum area and the at least one time domain feature includes a first difference power of the corrupted ECG waveform.

19. The patient monitoring device controller of claim 14,
wherein the feature extractor being configured to extract at least one frequency domain feature the segment of the corrupted ECG waveform includes the feature extractor configured to extract an amplitude spectrum area based frequency variable from the segment of the corrupted ECG waveform; and
wherein the asystole advisor being configured to detect the presence or the absence of the asystole rhythm within the segment of the corrupted ECG waveform as indicated by the least one frequency domain feature includes the asystole advisor configured to compare the amplitude spectrum area based frequency variable to at least one of an asystole detection threshold and a not-asystole detection threshold.

20. The patient monitoring device controller of claim 14,
wherein the feature extractor being configured to extract at least one time domain feature the segment of the corrupted ECG waveform includes the feature extractor configured to extract a first difference power based time variable from the segment of the corrupted ECG waveform; and
wherein the asystole advisor being configured to detect the presence or the absence of the asystole rhythm within the segment of the corrupted ECG waveform as indicated by the least one time domain feature includes the asystole advisor configured to compare the first difference power based time variable to at least one of an asystole detection threshold and a not-asystole detection threshold.

* * * * *